United States Patent [19]

DeMarinis et al.

[11] Patent Number: 5,639,748
[45] Date of Patent: Jun. 17, 1997

[54] 6,9-DISUBSTITUTED BENZAZEPINES HAVING α-ADRENOCEPTOR BLOCKING ACTIVITY

[75] Inventors: Robert Michael DeMarinis, Ardmore, Pa.; Francis Richard Pfeiffer, Cinnaminson, N.J.

[73] Assignee: SmithKline Beecham Corporation, King of Prussia, Pa.

[21] Appl. No.: 193,075

[22] PCT Filed: Aug. 5, 1992

[86] PCT No.: PCT/US92/06538

§ 371 Date: Feb. 4, 1994

§ 102(e) Date: Feb. 4, 1994

[87] PCT Pub. No.: WO93/03015

PCT Pub. Date: Feb. 18, 1993

[30] Foreign Application Priority Data

Aug. 5, 1991 [GB] United Kingdom ............... 9116824

[51] Int. Cl.$^6$ .................... A61K 31/55; C07D 401/12; C07D 403/12; C07D 405/12
[52] U.S. Cl. ............................ 514/213; 540/594
[58] Field of Search ............... 540/594; 514/213

[56] References Cited

U.S. PATENT DOCUMENTS

| | | | |
|---|---|---|---|
| 4,233,217 | 11/1980 | Shetty | 514/213 |
| 4,265,890 | 5/1981 | Holden et al. | 514/213 |
| 4,469,634 | 9/1984 | DeMarinis | 540/594 |
| 4,683,229 | 7/1987 | DeMarinis et al. | 540/594 |

FOREIGN PATENT DOCUMENTS 560235  9/1993  European Pat. Off. .

OTHER PUBLICATIONS

Medicinal Chemistry (2nd Ed.) by Alfred Burger (Editor), pp. 72–78 (1960).
Journal of Medicinal Chemistry, vol. 25, No. 12, pp. 1389–1401, 1982, Timmermans et al.
Journal of Medicinal Chemistry, vol. 27, No. 7, pp. 918–921, 1984, DeMarinis et al.

*Primary Examiner*—Emily Bernhardt
*Attorney, Agent, or Firm*—Mary E. McCarthy; Stephen Venetianer; Edward T. Lentz

[57] ABSTRACT

Alpha-adrenergic receptor antagonists having the formula:

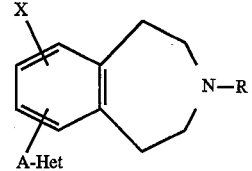

which are useful to produce α-adrenoceptor antagonism, pharmaceutical compositions including these antagonists, and methods of using these antagonists to produce α-adrenoceptor antagonism in mammals.

7 Claims, No Drawings

6,9-DISUBSTITUTED BENZAZEPINES HAVING α-ADRENOCEPTOR BLOCKING ACTIVITY

This application is a 371 of PCT/US92/06538 filed Aug. 5, 1992.

FIELD OF THE INVENTION

This invention relates to novel substituted 2,3,4,5-tetrahydro-1H-3-benzazepine compounds having α-adrenergic receptor antagonist activity.

BACKGROUND OF THE INVENTION

The autonomic nervous system is separated into the cholinergic and adrenergic nervous systems. Norepinephrine, the neurotransmitter of the adrenergic nervous system, exerts its activity by interaction with receptors (adrenoceptors) on the effector organs or on the nerve endings. The adrenoceptors are of two primary types: α and β. Based upon selectivity of the receptors for a series of agonists and antagonists, the a adrenoceptors have been subdivided into $\alpha_1$ and $\alpha_2$ subtypes.

A large amount of experimental evidence now supports the view that the $\alpha_2$ subtype is a heterogeneous adrenoceptor class. (For a general review see Timmermans and Van Zwieten, *J. Med. Chem.*, 25, 1389 (1982)). Experiments using 6-chloro-9-(3-methyl-2-butenyloxy)-3-methyl-2,3,4,5-tetrahydro-1H-3-benzazepine (SK&F 104078) demonstrated that the classical adrenoceptors are heterogeneous and can be divided into SK&F 104078-insensitive and SK&F 104078-sensitive $\alpha_2$ adrenoceptors. The latter variously are referred to as postjunctional $\alpha_2$ adrenoceptors or, preferably, $\alpha_3$ adrenoceptors, U.S. Pat. No. 4,683,229, Jul. 28, 1987.

As one of the primary regulators of peripheral vascular tone, α adrenoceptors long have been the targets of efforts to develop agents effective in changing vascular tone for use in treating diseases, such as hypertension, in which alterations in vascular resistance produce therapeutic benefits. Antihypertensive compounds presently in clinical use that function via interaction with a adrenoceptors include methyldopa, clonidine, and prazosin. Efforts to modulate sympathetic tone through interactions with a adrenoceptors have resulted in several compounds that interact somewhat selectively with $\alpha_1$ or $\alpha_2$ adrenoceptors. Selective agonists include phenylephrine and methoxamine which preferentially activate $\alpha_1$ receptors; and clonidine, α-methylnorepinephrine, and tramazoline which preferentially activate $\alpha_2$ adrenoceptors. Examples of selective α-adrenoceptor antagonists include prazosin which has high selectivity for $\alpha_1$ adrenoceptors; and the $\alpha_2$-selective blockers yohimbine and rauwolscine.

U.S. Pat. No. 4,469,634, dated Sep. 4, 1984, describes allyloxy- and allythio-2,3,4,5-tetrahydro-1H-3-benzazepines useful as intermediates for preparing $\alpha_2$ adrenoceptor affinity resins and as antihypertensive agents.

U.S. Pat. No. 4,683,229 dated Jul. 28, 1987, describes 6-halo-9-alkenyloxy-2,3,4,5-tetrahydro-1H-3-benzazepines having $\alpha_3$-selective antagonist activity.

U.S. Pat. No. 4,265,890 dated May 5, 1981, describes mercapto substituted-2,3,4,5-tetrahydro-1H-3-benzazepines having dopamine receptor blocking activity.

SUMMARY OF THE INVENTION

The present invention resides in the discovery that certain substituted-2,3,4,5,-tetrahydro-1H-3-benzazepine compounds are α-adrenoceptor antagonists. Presently preferred compounds of the invention include:

6-chloro-9-(3-furanylmethoxy)-2,3,4,5-tetrahydro-3-methyl-1H-3-benzazepine, 6-chloro-9-(4-chloro-1H-pyrazol-1-ylmethoxy)-2,3,4,5-tetrahydro-3-methyl-1H-3-benzazepine, 6-chloro-2,3,4,5-tetrahydro-3-methyl-9-(1H-pyrazol-1-ylmethoxy)-1H-3-benzazepine, 6-chloro-9-(2-furanylmethoxy)-2,3,4,5-tetrahydro-3-methyl-1H-3-benzazepine, 6-chloro-9-[3-(2-furanyl)-2-propenyloxy]-2,3,4,5-tetrahydro-3-methyl-1H-3-benzazepine, 6-chloro-2,3,4,5-tetrahydro-3-methyl-9-(2-thienylmethoxy)-1H-3-benzazepine, 6-chloro-2,3,4,5-tetrahydro-3 methyl-9-(3 thienylmethoxy)-1H-3-benzazepine, 6-chloro-2,3,4,5-tetrahydro-3 methyl-9-[2-(1H-pyrazol-1-yl)ethoxy]-1H-3-benzazepine, 6-chloro-2,3,4,5-tetrahydro-3-methyl -9-(1H-1,2,4-triazol-1-ylmethoxy)-1H-3-benzazepine, 6-chloro-2,3,4,5-tetrahydro-3-methyl-9-(4-pyridinylmethoxy)-1H-3-benzazepine, 6-chloro-2,3,4,5-tetrahydro-3-methyl-9-[2-(1H-1,2,4-triazol-1-yl)ethoxy]-1H-3-benzazepine, 6-chloro-9-[(4-chloro-1H-pyrazol-1-ylmethoxy)-methyl]-2,3,4,5-tetrahydro-3-methyl-1H-3-benzazepine, 6-chloro-9-[(4-chloro-1H-pyrazol-1-ylmethoxy)-carbonyl]-2,3,4,5-tetrahydro-3-methyl-1H-3-benzazepine, 6-chloro-2,3,4,5-tetrahydro-3-methyl-9-(1H-pyrrol-1-yl)-1H-3-benzazepine, 6-chloro-9-(2,5-dimethyl-1H-pyrrol-1-yl)-2,3,4,5-tetrahydro-3-methyl-1H-3-benzazepine, 6 chloro-2,3,4,5-tetrahydro-3-methyl-9-(1H-pyrrol-1-ylmethyl)-1H-3-benzazepine, 6-chloro-9-[5-(4-chloro-1H-pyrazol-1-yl)propyl]-2,3,4,5-tetrahydro-3-methyl-1H-3-benzazepine, and 6-chloro-9-[5-(4-chloro-1H-pyrazol-1-yl)pentyl]-2,3,4,5-tetrahydro-3-methyl-1H-3-benzazepine; or a pharmaceutically acceptable salt thereof.

The most preferred compound of the invention is 6-chloro-9-(3-furanylmethoxy)-2,3,4,5-tetrahydro-3-methyl-1H-3-benzazepine or a pharmaceutically acceptable salt thereof.

In a further aspect of the invention there are provided methods of antagonizing a adrenoceptors in mammals, including humans, that comprise administering internally to a subject an effective amount of a substituted 2,3,4,5-tetrahydro-1H-3-benzazepine compound.

Included in the present invention are pharmaceutical compositions comprising compounds useful in the method of the invention and a suitable pharmaceutical carrier. Preferably, these compositions are used to produce a adrenoceptor antagonism and contain an effective amount of compounds useful in the methods of the invention.

DETAILED DESCRIPTION OF THE INVENTION

The presently invented compounds that are α-adrenoceptor antagonists or are useful in preparing α-adrenoceptor antagonists are represented by the following Formula (I):

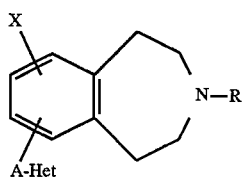

in which:

X is H, Cl, Br, F, I, CF$_3$, C$_{1-6}$alkyl, COR$^1$, CO2R$^2$, CONR$^2$R$^2$, CN, NO$_2$, NR$^3$R$^4$, OR$^3$, SR$^1$, SCF$_3$, or any accessible combination thereof up to three substituents;

R is H, C$_{1-6}$alkyl, or C$_{3-5}$alkenyl;

A is —OCO(CH$_2$)$_{1-4}$—, —OCH$_2$CH=CH—, —CO$_2$(CH$_2$)$_{1-4}$—, —(CH$_2$)$_{0-6}$—, or —(CH$_2$)$_n$Z(CH$_2$)$_m$—, wherein n is 0–4 and m is 1–5, with the proviso that m and n taken together are no greater than 5;

Z is O or S;

each R$^1$ independently is C$_{1-6}$alkyl or (CH$_2$)$_{0-6}$phenyl;

each R$^2$ independently is H, C$_{1-6}$alkyl, or (CH$_2$)$_{0-6}$phenyl;

R$^3$ is H, C$_{1-6}$alkyl, CHO, COR$^1$, or SO$_2$R$^1$;

R$^4$ is H or C$_{1-6}$alkyl; and

Het is a heteroaryl group selected from thienyl, furanyl, pyrazolyl, imidazolyl, pyrrolyl, triazolyl, oxazolyl, isoxazolyl, oxadiazolyl, thiadiazolyl, pyridazolyl, pyrimidinyl, pyrazolyl, thiazolyl, pyridinyl, or tetrazolyl which are unsubstituted or substituted by C$_{1-6}$alkyl, C$_{1-6}$alkoxy, Cl, Br, F, I, NR$^3$R$^4$, CO$_2$R$^2$, CONR$^2$R$^2$, CN, or NO$_2$;

or a pharmaceutically acceptable salt thereof, provided that when X is H, Cl, Br, F, CF$_3$, CH$_3$, OCH$_3$, OH, or OC(O)C$_{1-6}$alkyl, A-Het is not —S(CH$_2$)$_{0-1}$-thienyl or -furanyl.

As used herein C$_{1-6}$alkyl means straight or branched alkyl of one to six carbon atoms, C$_{3-5}$alkenyl means a straight or branched chain alkenyl having from 3 to 5 carbon atoms, and "any accessible combination thereof" means any combination of up to three substituents on the phenyl moiety that is available by chemical synthesis and is stable.

Formula (Ia) includes presently preferred Formula (I) compounds:

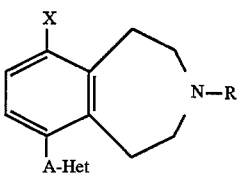

in which:

X is H, Cl, Br, F, I, CF$_3$, C$_{1-6}$alkyl, COR$^1$, CO$_2$R$^2$, CONR$^2$R$^2$, CN, NO$_2$, NR$^3$R$^4$, OR$^3$, or SCF3;

R is H, C$_{1-6}$alkyl, or C$_{3-5}$alkenyl;

A is —OCO(CH$_2$)$_{1-4}$—, —OCH$_2$CH=CH—, —CO$_2$(CH$_2$)$_{1-4}$—, —(CH$_2$)$_{0-6}$—, or —(CH$_2$)$_n$Z(CH$_2$)$_m$—, wherein n is 0–4 and m is 1–5, with the proviso that m and n taken together are no greater than 5;

Z is O or S;

each R$^1$ independently is C$_{1-6}$alkyl or (CH$_2$)$_{0-6}$phenyl;

each R$^2$ independently is H, C$_{1-6}$alkyl, or (CH$_2$)$_{0-6}$phenyl;

R$^3$ is H, C$_{1-6}$alkyl, CHO, COR$^1$, or SO$_2$R$^1$;

R$^4$ is H or C$_{1-6}$alkyl; and

Het is a heteroaryl group selected from thienyl, furanyl, pyrazolyl, imidazolyl, pyrrolyl, triazolyl, oxazolyl, isoxazolyl, thiazolyl, pyridinyl, or tetrazolyl, which are unsubstituted or substituted by C$_{1-6}$, C$_{1-6}$alkoxy, Cl, Br, F, I, NR$^3$R$^4$, CO$_2$R$^2$, CONR$^2$R$^2$, CN, or NO$_2$;

or a pharmaceutically acceptable salt thereof, provided that when X is H, Cl, Br, F, CF$_3$, CH$_3$, OCH$_3$, OH, or OC(O)C$_{1-6}$alkyl, A-Het is not —S(CH$_2$)$_{0-1}$-thienyl or -furanyl.

Preferred compounds are represented by Formula (Ia) when:

X is Cl, Br, F, or I;

R is CH$_3$; and

Het is pyrazolyl, furanyl, thienyl, triazolyl, pyridinyl, or pyrrolyl with each heteroaryl group being unsubstituted or substituted by Cl or CH$_3$.

Scheme I

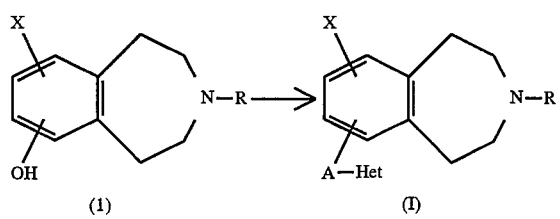

(1)                (I)

The benzazepines of formula (1) are described in published references, such as J. Med. Chem., 27: 918–921 (1984), or can be obtained readily using known procedures. According to Scheme I, the starting compounds of formula (1) are added to a suitable base, such as an alkali metal hydride, for example, sodium hydride, in a suitable organic solvent, such as dimethylformamide. Thereafter, an appropriately substituted halide or sulfonate, such as 3-(bromomethyl)furan, 2-(3-chloro-1-propenyl)furan, or 2-(1H-pyrazol-1-yl)ethyl 4-methylbenzenesulfonate, is reacted with the above-generated intermediate to produce Formula (I) compounds wherein A is —O(CH$_2$)$_m$— or —OCH$_2$CH=CH—.

Alternately, Formula (I) compounds wherein A is —O(CH$_2$)$_2$— are prepared by reacting the formula (1) benzazepine compounds with a suitable base, such as an alkali metal hydride, in a suitable solvent, such as dimethylformamide, followed by reaction with an ester of a haloacetate, such as ethyl bromoacetate. The resulting (benzazepinyl) oxy acetate ester is reduced to the corresponding alcohol using an appropriate reducing agent, such as lithium aluminum hydride, in an inert solvent, such as diethyl ether. Conversion of the alcohol to a suitable leaving group, such as a tosylate, or a mesylate, followed by displacement of the leaving group with an alkali metal salt of a heteroaryl group, such as 1H-1,2,4-triazole sodium salt, in a suitable solvent, such as dimethylformamide, gives the Formula (I) compounds wherein A is —O(CH$_2$)$_2$—.

Scheme II

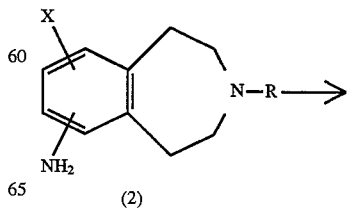

(2)

-continued
Scheme II

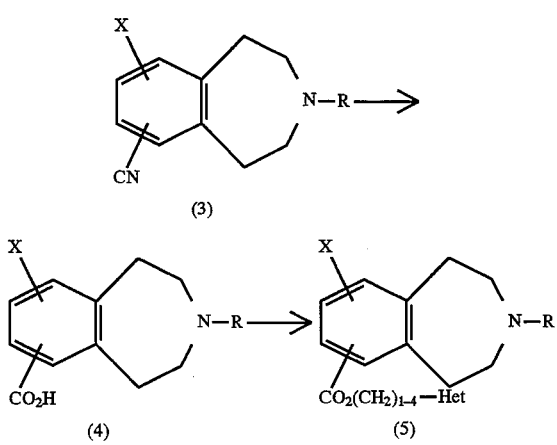

The benzazepines of formula (2) are known to the art (*J. Med. Chem.*, 27: 918–921 (1984)) or are synthesized by known procedures. According to Scheme II, the primary amine of formula (2) compounds is diazotized using, for example, sodium nitrite in acetic acid, water, and sulfuric acid. Conversion to the corresponding cyano compounds of formula (3) is accomplished by reacting the diazonium salt with cyanide, for example, potassium cyanide. The carboxylic acid compounds of formula (4) are prepared by reacting the cyano of the formula (3) compounds in the presence of barium hydroxide, in a suitable solvent, such as a mixture of ethanol and water. The resulting acids are reacted with a suitable base, such as an alkali metal hydride, such as sodium hydride, in an appropriate-solvent, such as dimethylformamide. Thereafter, reaction with an appropriately substituted halide, such as 4-chloro-1-(chloromethyl)-1H-pyrazole, gives formula (5) compounds, which are Formula (I) compounds wherein A is —CO$_2$(CH$_2$)$_{1-4}$—.

Formula (I) compounds wherein the heteroaryl group is directly attached to the phenyl portion of the benzazepine nucleus may be prepared from Formula (2) amine compounds. For example, the amine-substituted benzazepine compounds are reacted with 2,5-hexane-dione or 2,5-dimethoxytetrahydrofuran in a suitable solvent, such as acetic acid or a mixture of acetic acid and toluene, at a temperature of about 80° C. to about 120° C., preferably at about 110° C., to give pyrrole-substituted Formula (I) compounds.

Additionally, Formula (I) compounds wherein A is a methylene group may be prepared from formula (3) cyano compounds. The cyano group of the formula (3) benzazepines is reduced, for example, using lithium aluminum hydride, in an inert solvent, such as tetrahydrofuran, at a temperature of about 20° C. to about 75° C., preferably at about 70° C. The resulting methylamine compounds are then reacted with 2,5-hexane-dione or 2,5-dimethoxytetrahydrofuran, as described hereinbefore, to give, for example, Formula (I) compounds wherein A is —CH$_2$— and Het is a pyrrole moeity.

Scheme III

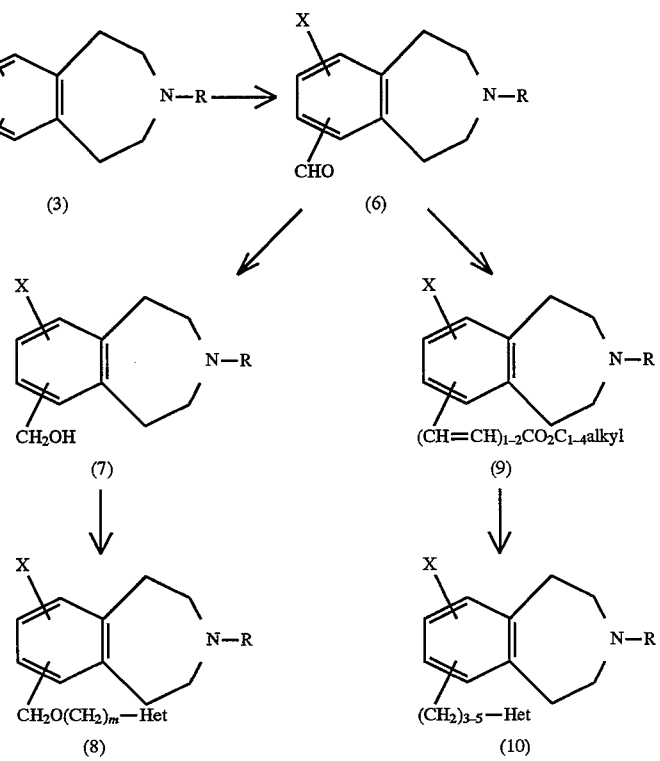

Scheme III illustrates the preparation of additional Formula (I) compounds. According to Scheme III, formula (3) cyano compounds are converted to the corresponding aldehyde derivatives of formula (6), for example using Raney® nickel in a suitable solvent, such as formic acid, at a temperature of about 35° C. to about 100° C., preferably at about 100° C. The formula (7) hydroxymethyl benzazepines are prepared from the formula (6) aldehyde compounds by reductive methods, for example, using sodium borohydride in a suitable solvent, such as methanol, at a temperature from about 0° C. to about 35° C., preferably from about 5° C. to about 24° C. Formula (8) benzazepines, which are Formula (I) compounds, are prepared from formula (7) benzazepines, using the methods described in Scheme I.

Scheme III also shows the preparation of Formula (I) compounds wherein A is —$(CH_2)_{3-5}$—. According to Scheme III, formula (6) aldehyde compounds are reacted with a phosphorus ylide, such as triphenylphosphoranylideneacetaldehyde, in a suitable solvent, such as toluene, at a temperature of about 80° C. to about 110° C., preferably at 110° C., or with an alkylphosphonic ester, such as triethyl phosphonoacetate, which is converted to a phosphonate carbanion in reaction with a suitable base, such as sodium hydride, in a suitable solvent, such as tetrahydrofuran, to give the corresponding alkenyl derivatives, for example —CH=CH—CH=CH—CHO or —CH=CHCO$_2$ethyl, respectively. The vinyl intermediates thus generated are reduced to the corresponding saturated analogs, for example by hydrogenation in the presence of a suitable catalyst, such as platinum oxide, in a suitable solvent, such as ethanol. The terminal ester or formyl groups are reduced to the corresponding alcohol derivatives using standard reagents, for example, an ester-reducing agent, such as lithium aluminum hydride, or a formyl-reducing agent, such as sodium borohydride. The alcohols are reacted with a halogenating agent, such as thionyl chloride, to give —$(CH_2)_{3-5}$halo benzazepines. Displacement of the halide by an alkali metal salt of a heteroaryl group, such as 1H-1,2,4-triazole sodium salt, gives Formula (I) compounds wherein A is —$(CH_2)_{3-5}$—.

The pharmaceutically acceptable, nontoxic, acid addition salts having the utility of the free bases of Formula (I), are formed with inorganic or organic acids, by methods well known in the art. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

Because the compounds of Formula (I) are α-adrenoceptor antagonists they are useful in treating cardiovascular diseases in which changes in vascular resistance are desirable, including hypertension, pulmonary hypertension, congestive heart failure, myocardial ischemia, and angina pectoris. Formula (I) compounds also are useful in treating peripheral vascular disease, benign prostatic hypertrophy, diabetes, glaucoma, ocular hypertension, obesity, disorders of gastrointestinal motility, including colonic spasm, irritable bowel syndrome, and constipation, impotence, and central nervous system disorders such as depression and senile dementia. Additionally, the invented compounds are useful in treating diseases resulting from inappropriate platelet aggregation.

The α-adrenoceptor activity of certain compounds of the present invention was determined using the following in vitro systems.

Alpha$_1$ adrenoceptor antagonist activity was determined using the rabbit aorta. Male New Zealand White rabbits (2–4 Kg) were euthanized by cervical concussion. A 4 cm portion of the thoracic aorta was removed and placed in a dish of cold (10° C.) Krebs-Hensleit solution. The tissue was cleaned of fat and connective tissue and cut into segments of approximately 3 mm in length. These segments were suspended in 10 ml tissue baths via hangers constructed of 0.25 mm tungsten wire. One hanger was fixed to a support in the bath and the other was attached via silk thread to a force-displacement transducer.

Tissue segments were equilibrated for 2 hours prior to drug testing, during which time basal tension was maintained at 2 gm. Tissues were washed at 30 minute intervals during this equilibration period. The Krebs-Hensleit solution contained cocaine (6 mM) to block neuronal uptake and propranolol (1 mM) to block beta-adrenoceptors. Tissues were usually challenged once with norepinephrine (0.1 mM) during the equilibration period to check for viability.

A cumulative concentration-response curve to norepinephrine was obtained in each aortic segment. Following washout of norepinephrine, the α adrenoceptor antagonist to be tested was added to the bath. After the tissue had been in contact with the antagonist for 30–60 minutes, the norepinephrine concentration response-curve was repeated in the presence of antagonist. The tissue was then washed again, and a tenfold higher concentration of antagonist added. Following equilibration (30–60 minutes), a third norepinephrine concentration-response curve was determined in the presence of the antagonist.

The receptor dissociation constant ($K_\beta$) for the antagonist was determined using the relationship $$K_\beta = \frac{\text{Antagonist Concentration}}{\text{Dose Ratio} - 1}$$

(Furchgott, R. F., *Handbook of Experimental Pharmacology*, eds. Eichler, et al., pp. 283–335 (Springer 1972)). The $K_\beta$ value obtained at each antagonist concentration was averaged to obtain a mean $K_\beta$ for each experiment.

Alpha$_2$ adrenoceptor antagonist activity of the compounds was determined using the isolated, superfused guinea pig left atrium. Briefly, the heart is removed from a pentobarbital-anesthetized male guinea pig. The left atrium is separated, dissected free of extraneous tissue and mounted in a 2 ml superfusion chamber. The tissue is paced at 30 pulse/minute and the sympathetic nerves excited at 6 minute intervals by field stimulation. The response to nerve stimulation is measured as the difference in contractile force between the basal contraction and peak contraction following a nerve stimulation. A concentration-response curve for B-HT 920 (a known α$_2$ agonist) is prepared by administering increasing concentrations of B-HT 920 following each successive stimulation. The tissue then is superfused for thirty minutes with the α-adrenoceptor antagonist to be tested and the B-HT 920 concentration-effect curve is repeated in the presence of antagonist. Data are reported as $K_B$, defined above. Additional details of this test system are found in Hieble, J. P. and R. G. Pendleton, *Arch. Pharmacol.*, 309: 217–224 (1979).

Alpha$_3$ adrenoceptor antagonist receptor activity was determined using the dog saphenous vein (DSV) as the test system. This test system has been shown a suitable preparation in which to characterize postsynaptic α$_2$(α$_3$) adrenoceptors, Sullivan, A. T. and G. M. Drew, *Arch. Pharmacol.*, 314: 249–58 (1980). This test system is prepared by removing the lateral saphenous vein from an anesthetized dog and cutting the vein into segments of 4 mm in length. Segments are mounted as described for the isolated rabbit aorta.

The α$_3$ adrenoceptor antagonist activity of the compounds of interest is determined by measuring shifts in the dose-response curve of a specific agonist induced by the tested compounds. The α$_2$, α$_3$ agonist, B-HT 920, was used in testing the compounds listed in Table I.

Representative Formula (I) compounds which were tested using the above described in vitro test systems are listed in Table I. Each of the compounds tested was found to have antagonist activity at one or more of the α-adrenoceptor subtypes.

TABLE I 6-chloro-9-(4-chloro-1H-pyrazol-1-ylmethoxy)-2,3,4,5-tetrahydro-3-methyl-1H-3-benzazepine;
6-chloro-2,3,4,5-tetrahydro-3-methyl-9-(1H-pyrazol-1-ylmethoxy)-1H-3-benzazepine;
6-chloro-9-(2-furanylmethoxy)-2,3,4,5-tetrahydro-3-methyl-1H-3-benzazepine;
6-chloro-9-(3-furanylmethoxy)-2,3,4,5-tetrahydro-3-methyl-1H-3-benzazepine;
6-chloro-9-[3-(2-furanyl)-2-propenyloxy]-2,3,4,5-tetrahydro-3-methyl-1H-3-benzazepine;
6-chloro-2,3,4,5-tetrahydro-3-methyl-9-(2-thienylmethoxy)-1H-3-benzazepine;
6-chloro-2,3,4,5-tetrahydro-3-methyl-9-(3-thienylmethoxy)-1H-3-benzazepine;
6-chloro-2,3,4,5-tetrahydro-3-methyl-9-[2-(1H-pyrazol-1-yl)ethoxy]-1H-3-benzazepine
6-chloro-2,3,4,5-tetrahydro-3-methyl-9-(1H-1,2,4-triazol-1-ylmethoxy)-1H-3-benzazepine;
6-chloro-2,3,4,5-tetrahydro-3-methyl-9-(4-pyridinylmethoxy)-1H-3-benzazepine;
6-chloro-2,3,4,5-tetrahydro-3-methyl-9-[2-(1H-1,2,4-triazol-1-yl)ethoxy]-1H-3-benzazepine;
6-chloro-9-[(4-chloro-1H-pyrazol-1-ylmethoxy)-methyl]-2,3,4,5-tetrahydro-3-methyl-1H-3-benzazepine;
6-chloro-9-[(4-chloro-1H-pyrazol-1-ylmethoxy)-carbonyl]-2,3,4,5-tetrahydro-3-methyl-1H-3-benzazepine;
6-chloro-2,3,4,5-tetrahydro-3-methyl-9-(1H-pyrrol-1-yl)-1H-3-benzazepine;
6-chloro-9-(2,5-dimethyl-1H-pyrrol-1-yl)-2,3,4,5-tetrahydro-3-methyl-1H-3-benzazepine;
6-chloro-2,3,4,5-tetrahydro-3-methyl-9-(1H-pyrrol-1-ylmethyl)-1H-3-benzazepine;
6-chloro-9-[3-(4-chloro-1H-pyrazol-1-yl)propyl]-2,3,4,5-tetrahydro-3-methyl-1H-3-benzazepine; and
6-chloro-9-[5-(4-chloro-1H-pyrazol-1-yl)pentyl]-2,3,4,5-tetrahydro-3-methyl-1H-3-benzazepine; or a pharmaceutically acceptable salt thereof.

The antihypertensive activity of certain compounds of the present invention was determined using the spontaneously hypertensive rat model. The details of this in vivo test are found in Roesler, J. M., et al., *J. Pharmacol. Exp. Ther.*, 236: 1–7 (1986).

Novel pharmaceutical compositions are obtained when the compounds are incorporated with pharmaceutical carriers into convenient dosage forms such as capsules, tablets, or injectable preparations. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid, or an aqueous or nonaqueous liquid suspension or solution.

The pharmaceutical preparations are made following conventional techniques of a pharmaceutical chemist involving mixing, granulating and compressing, when necessary, for tablet forms, or mixing,, filling, and dissolving the ingredients, as appropriate, to give the desired oral or parenteral products.

Doses of the present compounds in pharmaceutical dosage units will be an efficacious, nontoxic quantity selected from the range of 0.01–100 mg/kg of active compound, preferably 0.1–50 mg/kg. The selected dose is administered to a human patient in need of treatment from 1–6 times daily, orally, rectally, topically, by inhalation, or injection, or continuously by infusion. Oral administration, however, is preferred because it is more convenient for the patient.

The following examples are illustrative of preparation of Formula (I) compounds. The examples are not intended to limit the scope of the invention as defined hereinabove and as claimed below.

EXAMPLE 1

6-Chloro-9-(4-chloro-1H-pyrazol-1-ylmethoxy)-2,3,4,5-tetrahydro-3-methyl-1H-3-benzazepine A solution of 9-chloro-2,3,4,5-tetrahydro-3-methyl-1H-3-benzazepin-6-ol, (633 mg, 3 mmol, *J. Med. Chem.*, 27, 918 (1984)) in dry dimethylformamide (10 ml) was treated with sodium hydride (50% dispersion in mineral oil, 3.9 mmol), stirred for 10 minutes and treated with a solution of 4-chloro-1-(chloromethyl)-1-pyrazole (485 mg, 3.1 mmol) in dimethylformamide (5 ml). The mixture was heated to 50° C. for 30 minutes, poured into ice water, basified with 10% sodium hydroxide and extracted with ethyl acetate. The organic phase was washed with brine, dried with magnesium sulfate and concentrated. The residue was treated with hydrogen chloride in ethanol-ethyl ether to give 275 mg (26%) of 6-chloro-9-(4-chloro-1H-pyrazol-1-ylmethoxy)-2,3,4,5-tetrahydro-3-methyl-1H-3-benzazepine hydrochloride (acetone); mp 174°–175° C.

EXAMPLE 2

6-Chloro-2,3,4,5-tetrahydro-3-methyl-9-(1H-pyrazol-1-ylmethoxy)-1H-3-benzazepine Using the general procedure of Example 1, replacing 4-chloro-1-(chloromethyl)-1H-pyrazole with 1-(chloromethyl)-1-pyrazole gave, after chromatography on silica gel eluted with a methanol-methylene chloride gradient, 6-chloro-2,3,4,5-tetrahydro-3-methyl-9-(1H-pyrazol-1-ylmethoxy)-1H-3-benzazepine; mp 69°–71.5° C.

EXAMPLES 3–10

6-Chloro-9-(2-furanylmethoxy)-2,3,4,5-tetrahydro-3-methyl-1H-3-benzazepine

6-Chloro-9-(3-furanylmethoxy)-2,3,4,5-tetrahydro-3-methyl-1H-3-benzazepine

6-Chloro-9-[3-(2-furanyl)-2-propenyloxy]-2,3,4,5-tetrahydro-3-methyl-1H-3-benzazepine 6-Chloro-2,3,4,5-tetrahydro-3-methyl-9-(2-thienylmethoxy)-1H-3-benzazepine 6-Chloro-2,3,4,5-tetrahydro-3-methyl-9-(3-thienylmethoxy)-1H-3-benzazepine 6-Chloro-2,3,4,5-tetrahydro-3-methyl-9-[2-(1H-pyrazol-1-yl) ethoxy]-1H-3-benzazepine 6-Chloro-2,3,4,5-tetrahydro-3-methyl-9-(1H-1,2,4-triazol-1-ylmethoxy)-1H-3-benzazepine 6-Chloro-2,3,4,5-tetrahydro-3-methyl-9-(4-pyridinylmethoxy)-1H-3-benzazepine Using the general procedure of Example 2, replacing 1-(chloromethyl)-1H-pyrazole with 2-(chloromethyl)furan, 3-(bromomethyl) furan, 2-(3-chloro-1-propenyl)furan, 2-(bromomethyl)thiophene, 3-(bromomethyl)thiophene, 2-(1H-pyrazol-1-yl)ethyl 4-methylbenzenesulfonate, 1-(chloro-methyl)-1H-1,2,4-triazole, and 4-(chloromethyl) pyridine hydrochloride gave:

- 6-chloro-9-(2-furanylmethoxy)-2,3,4,5-tetrahydro-3-methyl-1H-3-benzazepine maleate; mp 168°–173.5° C.,
- 6-chloro-9-(3-furanylmethoxy)-2,3,4,5-tetrahydro-3-methyl-1H-3-benzazepine maleate; mp 181°–183° C.,
- 6-chloro-9-[3-(2-furanyl)-2-propenyloxy]-2,3,4,5-tetrahydro-3-methyl-1H-3-benzazepine maleate; mp 149°–153.5° C.,
- 6-chloro-2,3,4,5-tetrahydro-3-methyl-9-(2-thienylmethoxy)-1H-3-benzazepine maleate; 196.5°–199.5° C.,
- 6-chloro-2,3,4,5-tetrahydro-3-methyl-9-(3-thienylmethoxy)-1H-3-benzazepine maleate; mp 195.5°–198.5° C.,
- 6-chloro-2,3,4,5-tetrahydro-3-methyl-9-[2-(1H-pyrazol-1-yl)ethoxy]-1H-3-benzazepine hydrochloride; mp 98°–180° C.,
- 6-chloro-2,3,4,5-tetrahydro-3-methyl-9-(1H-1,2,4-triazol-1-ylmethoxy)-1H-3-benzazepine hydrochloride; mp 82°–92.5° C., and
- 6-chloro-2,3,4,5-tetrahydro-3-methyl-9-(4-pyridinylmethoxy)-1H-3-benzazepine dihydrochloride (ethanolethyl acetate); mp 222° C. (dec).

EXAMPLE 11

6-Chloro-2,3,4,5-tetrahydro-3-methyl-9-[2-(1H-1,2,4-triazol-1-yl)ethoxy]-1H-3-benzazepine A 35% dispersion of potassium hydride in mineral oil (2.6 g, 23 mmol) in dimethylformamide (40 ml) was stirred and treated with 9-chloro-2,3,4,5-tetrahydro-3-methyl-1H-3-benzazepin-6-ol (4.0 g, 19 mmol), stirred for 20 minutes, treated with ethyl bromoacetate (3.8 g, 23 mmol) and stirred for 72 hours. The mixture was concentrated, partitioned between water and methylene chloride and the organic phase was washed, dried with magnesium sulfate and concentrated. The residue was chromatographed on silica gel eluted with methanol-methylene chloride (8:92) to give 4.3 g of ethyl [(9-chloro-2,3,4,5-tetrahydro-3-methyl-1H-3-benzazepin-6-yl)oxy]acetate.

Lithium aluminum hydride (1.53 g, 40 mmol) in ethyl ether (80 ml) was stirred, heated to reflux and treated with a solution of ethyl [(9-chloro-2,3,4,5-tetrahydro-3-methyl-1H-3-benzazepin-6-yl)oxy]acetate (4.0 g, 13.5 mmol) in ethyl ether (60 ml). The mixture was stirred at reflux for 3.5 hours, cooled, and carefully treated with water (1.5 ml), 10% sodium hydroxide (4.5 ml) and water (1.5 ml). The mixture was filtered and the filtrate dried with magnesium sulfate and concentrated to give 3.2 g (91%) of [(9-chloro-2,3,4,5-tetrahydro-3-methyl-1H-3-benzazepin-6-yl)oxy]ethanol.

A solution of [(9-chloro-2,3,4,5-tetrahydro-3-methyl-1H-3-benzazepin-6-yl)oxy]ethanol (0.375 g, 1.5 mmol) in pyridine (5 ml) was stirred at 5° C., treated with 4-methylbenzenesulfonyl chloride (0.56 g, 3 mmol) and stored in a freezer for 16 hours. The mixture was poured into water and extracted with ethyl ether. The organic phase was washed and concentrated under high vacuum to give 0.5 g of [(9-chloro-2,3,4,5-tetrahydro-3-methyl-1-3-benzazepin-6-yl) oxy]ethanol 4-methylbenzenesulfonate.

Following the general procedure of Example 2, [(9-chloro-2,3,4,5-tetrahydro-3-methyl-1H-3-benzazepin-6-yl) oxy]ethanol 4-methylbenzenesulfonate was heated with one equivalent of 1H-1,2,4-triazole sodium salt (prepared from 1H-1,2,4-triazole and sodium hydride in dimethylformamide) at 65° C. for 30 minutes to give 6-chloro-2,3,4,5-tetrahydro-3-methyl-9-[2-(1H-1,2,4-triazol-1-yl)ethoxy]-1H-3-benzazepine hydrochloride; mp 204°–211° C.

EXAMPLE 12

6-Chloro-9-[(4-chloro-1H-pyrazol-1-ylmethoxy) methyl]-2,3,4,5-tetrahydro-3-methyl-1H-3-benzazepine A solution of 9-chloro-2,3,4,5-tetrahydro-3-methyl-1H-3-benzazepin-6-amine, (10 g, 47.5 mmol) in acetic acid (34 ml) and water (20 ml) was stirred, treated with sulfuric acid (7.5 ml), cooled to 5° C. and treated with a solution of sodium nitrite (3.65 g, 53 mmol) in water (7.5 ml) added below the surface over 20 minutes. The mixture was added dropwise under the surface of a stirred mixture prepared from cupric sulfate pentahydrate (14.2 g, 57 mmol) in water (35 ml), potassium cyanide (15.4 g, 240 mmol), ice (24 g), sodium bicarbonate (31.8 g, 380 mmol) in water (36 ml) and toluene (35 ml) at 50°–55° C. The mixture was stirred for 15 minutes at 50° C. and for 1 hour at 25° C., treated with a solution of sodium bicarbonate (70 g) in water (700 ml) to pH 8 and then with 10% sodium hydroxide (300 ml). The mixture was extracted with ethyl acetate and the organic phase was washed with aqueous sodium hydroxide and brine, dried with magnesium sulfate and concentrated. The residual oil was treated with ethereal hydrogen chloride to give 8.3 g (68%) of 9-chloro-2,3,4,5-tetrahydro-3-methyl-1H-3-benzazepine-6-carbonitrile; mp 288°–290° C.

A solution of 9-chloro-2,3,4,5-tetrahydro-3-methyl-1H-3-benzazepine-6-carbonitrile (3.1 g, 14 mmol) in 90% formic acid (40 ml) was treated with Raney® nickel (3.1 g), stirred and heated to reflux for 3 hours. Additional Raney® nickel (17 g) and 90% formic acid (85 ml) were added over the next 12 hours and the mixture was stirred for an additional 3 hours. The mixture was cooled, filtered and the filter cake washed with 45% formic acid. The filtrate was concentrated, basified with 10% sodium hydroxide, extracted with ethyl acetate and the organic phase was washed, dried and concentrated to give 3 g of 9-chloro-2,3,4,5-tetrahydro-3-methyl-1H-3-benzazepine-6-carboxaldehyde.

A solution of 9-chloro-2,3,4,5-tetrahydro-3-methyl-1H-3-benzazepine-6-carboxaldehyde (3.07 g, 13.8 mmol) in methanol (35 ml) was cooled to 5° C. and treated with sodium borohydride (3.07 g, 81 mmol). The mixture was stirred for 15 minutes at 5° C. and for 45 minutes at 25° C. The mixture was cooled and carefully treated with dilute hydrochloric acid. The mixture was diluted with brine, basified with 10% sodium hydroxide and extracted with ethyl acetate. The organic phase was dried, concentrated and the residue chromatographed on silica gel eluted with a gradient of methanol-methylene chloride (5:95–9:91) to give 1.45 g (47%) of 9-chloro-2,3,4,5-tetrahydro-3-methyl-1H-3-benzazepine-6-methanol; mp 136.5°–140° C.

Using the general procedure of Example 1, replacing 9-chloro-2,3,4,5-tetrahydro-1H-3-benzazepin-6-ol with 9-chloro-2,3,4,5-tetrahydro-3-methyl-1H-3-benzazepine-6-methanol gave, after chromatography on silica gel eluted with methanol-methylene chloride (4:96), 0.3 g (40%) of 6-chloro-9-[(4-chloro-1H-pyrazol-1-ylmethoxy)methyl]-2,3,4,5-tetrahydro-3-methyl-1H-3-benzazepine hydrochloride; mp 168°–171° C.

EXAMPLE 13

6-Chloro-9-[(4-chloro-1H-pyrazol-1-ylmethoxy) carbonyl]-2,3,4,5-tetrahydro-3-methyl-1H-3-benzazepine A solution of 9-chloro-2,3,4,5-tetrahydro-3-methyl-1H-3-benzazepine-6-carbonitrile, prepared as in Example 12, (1.5 g, 6.8 mmol) in ethanol (25 ml) was treated with barium hydroxide octahydrate (2.6 g, 8.1 mmol) and water (25 ml) and heated to reflux for 94 hours. The mixture was cooled, diluted with water, ethanol and methanol, saturated with carbon dioxide and filtered. The filtrate was treated with Dry Ice to pH 5–6 and filtered. The filtrate was concentrated and extracted with ethyl acetate-ethyl ether and ethyl ether. The aqueous phase was treated with toluene, concentrated and the residue triturated with ethyl ether to give 9-chloro-2,3,4,5-tetrahydro-1H-3-benzazepine-6-carboxylic acid.

Using the general procedure of Example 1, replacing 9-chloro-2,3,4,5-tetrahydro-1H-3-benzazepin-6-ol with 9-chloro-2,3,4,5-tetrahydro-1H-3-benzazepine-6-carboxylic acid gave, after chromatography on silica gel eluted with methanol-methylene chloride (3:97), 94 mg (10%) of 6-chloro-9-[(4-chloro-1H-pyrazol-1-ylmethoxy)carbonyl]-2,3,4,5-tetrahydro-3-methyl-1H-3-benzazepine maleate; mp 144°–149° C.

EXAMPLE 14

6-Chloro-2,3,4,5-tetrahydro-3-methyl-9-(1H-pyrrol-1-yl)-1H-3-benzazepine

A solution of 9-chloro-2,3,4,5-tetrahydro-3-methyl-1H-3-benzazepin-6-amine (633 mg, 3 mmol) in acetic acid (6 ml) was treated with 2,5-dimethoxytetrahydrofuran (396 mg, 3 mmol) and stirred at 110° C. for 1.5 hours. The mixture was poured into ice, basified with 10% sodium hydroxide and extracted with ethyl acetate. The organic phase was dried, concentrated and treated with hydrogen chloride to give 6-chloro-2,3,4,5-tetrahydro-3-methyl-9-(1H-pyrrol-1-yl)-1H-3-benzazepine hydrochloride (methanol-acetonitrile); mp 262°–264° C.

EXAMPLE 15

6-Chloro-9-(2,5-dimethyl-1-pyrrol-1-2,3,4,5-tetrahydro-3-methyl-1H-3-benzazepine Using the general procedure of Example 40, 9-chloro-2,3,4,5-tetrahydro-3-methyl-1H-3-benzazepin-6-amine (420 mg, 2.7 mmol) in acetic acid (6 ml) and toluene (6 ml) was treated with 2,5-hexanedione (300 mg, 2.7 mmol) and heated to reflux for 1 hour to give 6-chloro-9-(2,5-dimethyl-1H-pyrrol-1-yl)-2,3,4,5-tetrahydro-3-methyl-1-3-benzazepine (acetonitrile); mp 268°–270° C.

EXAMPLE 16

6-Chloro-2,3,4,5-tetrahydro-3-methyl-9-(1H-pyrrol-1-ylmethyl)-1H-3-benzazepine A suspension of lithium aluminum hydride (1.14 g, 30 mmol) in tetrahydrofuran (20 ml) was stirred and treated with a solution of 9-chloro-2,3,4,5-tetrahydro-3-methyl-1H-3-benzazepine-6-carbonitrile, prepared as in Example 12, (1.5 g, 6.8 mmol) in tetrahydrofuran (20 ml) and heated to reflux for 3 hours. The mixture was cooled and treated with water (1.14 ml), 10% sodium hydroxide (1.14 ml) and water (1.14 ml), diluted with tetrahydrofuran (100 ml), stirred for 1 hour, filtered and concentrated to give 9-chloro-2,3,4,5-tetrahydro-3-methyl-1-3-benzazepine-6-methanamine.

A solution of 9-chloro-2,3,4,5-tetrahydro-3-methyl-1H-3-benzazepine-6-methanamine (0.75 g, 3.4 mmol) in acetic acid (6.5 ml) was treated with 2,5-dimethoxytetrahydrofuran (0.44 ml, 3.4 mmol) and heated to 115° C. for 1 hour. The mixture was quenched with ice water, basified with 20% sodium hydroxide and extracted with ethyl acetate. The organic phase was washed, dried and concentrated. The residue was triturated with ethyl ether and the residue chromatographed on silica gel eluted with methanol-methylene chloride (3:97) to give 6-chloro-2,3,4,5-tetrahydro-3-methyl-9-(1H-pyrrol-1-ylmethyl)-1H-3-benzazepine hydrochloride; mp 219°–223° C.

EXAMPLE 17

6-Chloro-9-[3-(4-chloro-1H-pyrazol-1-yl)propyl]-2,3,4,5-tetrahydro-3-methyl-1H-3-benzazepine A solution of triethyl phosphonoacetate (1.9 g, 8.6 mmol) in tetrahydrofuran (200 ml) was stirred and treated with a 50% dispersion of sodium hydride in mineral oil (0.45 g, 9.4 mmol), stirred for 15 minutes and treated with a solution of 9-chloro-2,3,4,5-tetrahydro-3-methyl-1H-3-benzazepine-6-carboxaldehyde, prepared as in Example 12, (2.2 g, 9.0 mmol) in tetrahydrofuran (270 ml). The mixture was stirred for 16 hours, concentrated, dissolved in ethyl ether and washed with water and brine. The organic phase was dried with magnesium sulfate and concentrated to give 2.6 g of ethyl (E)-3-(9-chloro-2,3,4,5-tetrahydro-3-methyl-1H-3-benzazepin-6-yl)-2-propenoate.

A solution of ethyl (E)-3-(9-chloro-2,3,4,5-tetrahydro-3-methyl-1-3-benzazepin-6-yl)-2-propenoate (2.6 g, 8.9 mmol) in ethanol (150 ml) was treated with concentrated hydrochloric acid (18 drops) and platinum oxide (0.11 g) and shaken under hydrogen (40 psi) for 2 hours, filtered and concentrated. The residue was partitioned between cooled ethyl acetate-ethyl ether (3:1) (300 ml) and 5% sodium bicarbonate. The organic phase was washed with water and brine, dried with magnesium sulfate and concentrated to give 2.5 g (96%) of ethyl 9-chloro-2,3,4,5-tetrahydro-3-methyl-1H-3-benzazepine-6-propenoate.

A suspension of lithium aluminum hydride (0.55 g, 14.6 mmol) in tetrahydrofuran (20 ml) was stirred, heated to reflux and treated with a solution of ethyl 9-chloro-2,3,4,5-tetrahydro-3-methyl-1H-3-benzazepine-6-propenoate (2.1 g, 7 mmol) in tetrahydrofuran (25 ml). The mixture was stirred at reflux for 3 hours, cooled and carefully treated with water (1.65 ml) and 10% sodium hydroxide (0.55 ml). The mixture was stirred at 25° C., filtered and the filtrate was concentrated. The residue was dissolved in ethyl acetate-ethyl ether (4:1) (160 ml) and washed with water, 5% sodium hydroxide and water, filtered, dried with magnesium sulfate and concentrated. The residue was partitioned between ethyl acetate-ethyl ether (2:1) and 3N hydrochloric acid. The aqueous phase was washed with ethyl ether, basified with aqueous sodium hydroxide and extracted with ethyl acetate-ethyl ether (2:1). The organic phase was washed with water and brine, dried with magnesium sulfate and concentrated. The residue was dissolved in ethyl ether and treated with ethereal hydrogen chloride to give 9-chloro-2,3,4,5-tetrahydro-3-methyl-1H-3-benzazepine-6-propanol hydrochloride; mp 218.5°–223.5° C.

A solution of 9-chloro-2,3,4,5-tetrahydro-3-methyl-1H-3-benzazepine-6-propanol (0.8 g, 3 mmol) in methylene chloride (30 ml) was stirred at 5° C. and treated with thionyl chloride (40 ml). The mixture was stirred for 10 minutes at 5° C., 15 minutes at 25° C., 3 hours at 55° C. and 16 hours at 25° C. The mixture was concentrated to give 0.96 g of 6-chloro-9-(3-chloropropyl)-2,3,4,5-tetrahydro-3-methyl-1H-3-benzazepine hydrochloride.

Using the general procedure of Example 11, replacing [(9-chloro-2,3,4,5-tetrahydro-3-methyl-1H-3-benzazepin-6-yl)oxy]ethanol 4-methylbenzenesulfonate with 6-chloro-9-(3-chloropropyl)-2,3,4,5-tetrahydro-3-methyl-1H-3-benzazepine and 1H-1,2,4-triazole sodium salt with 4-chloro-1H-pyrazole gave 0.33 g (60%) of 6-chloro-9-[3-(4-chloro-1H-pyrazol-1-yl)propyl]-2,3,4,5-tetrahydro-3-methyl-1H-3-benzazepine hydrochloride; mp 142.5°–145° C.

EXAMPLE 18

6-Chloro-9-[5-(4-chloro-1H-pyrazol-1-yl)pentyl]-2,3,4,5-tetrahydro-3-methyl-1H-3-benzazepine A solution of 9-chloro-2,3,4,5-tetrahydro-3-methyl-1H-3-benzazepine-6-carboxaldehyde, prepared as in Example 12, (2.2 g, 10 mmol) in toluene (15 ml) was treated with triphenylphosphoranylideneacetaldehyde (4.4 g, 14 mmol) and stirred at 100° C. for 24 hours. The mixture was concentrated and the residue was triturated with ethyl ether-petroleum ether (4:1) and the supernatant concentrated to give 3 g of 5-(9-chloro-2,3,4,5-tetrahydro-3-methyl-1H-3-benzazepin-6-yl)-2,4-pentadienal.

A solution of 5-(9-chloro-2,3,4,5-tetrahydro-3-methyl-1H-3-benzazepin-6-yl)-2,4-pentadienal (3 g) in ethanol (100 ml) and platinum oxide was shaken under hydrogen (50 psi) for 2 hours, filtered, concentrated and the residue chromatographed on silica gel eluted with a gradient of methanol-methylene chloride (3:97°–7:93) to give 0.5 g of 9-chloro-2,3,4,5-tetrahydro-3-methyl-1H-3-benzazepine-6-pentanal.

Using the general procedure of Example 12, replacing 9-chloro-3-methyl-2,3,4,5-tetrahydro-1-3-benzazepine-6-carboxaldehyde with 9-chloro-2,3,4,5-tetrahydro-3-methyl-1H-3-benzazepine-6-pentanol gave 0.33 g (64%) of 9-chloro-2,3,4,5-tetrahydro-3-methyl-1H-3-benzazepine-6-pentanol.

Using the general procedure of Example 43, replacing 9-chloro-2,3,4,5-tetrahydro-3-methyl-1H-3-benzazepine-6-propanol with 9-chloro-2,3,4,5-tetrahydro-3-methyl-1H-3-benzazepine-6-pentanol gave 6-chloro-9-(5-chloropentyl)-2,3,4,5-tetrahydro-3-methyl-1H-3-benzazepine hydrochloride.

Using the general procedure of Example 43, replacing 6-chloro-9-(3-chloropropyl)-2,3,4,5-tetrahydro-3-methyl-1H-3-benzazepine with 6-chloro-9-(5-chloropentyl)-2,3,4,5-tetrahydro-3-methyl-1H-3-benzazepine gave 52 mg (13%) of 6-chloro-9-[5-(4-chloro-1H-pyrazol-1-yl)pentyl]-2,3,4,5-tetrahydro-3-methyl-1H-3-benzazepine hydrochloride; mp 158°–161° C.

EXAMPLE 19

An oral dosage form for administering the presently invented compounds is produced by screening, mixing, and filling into a hard gelatin capsule ingredients in the proportions shown in Table II, below.

TABLE II

| Ingredients | Amounts |
| --- | --- |
| 6-chloro-9-(3-furanylmethoxy)-2,3,4,5-tetrahydro-3-methyl-1H-3-benzazepine | 50 mg |
| magnesium stearate | 5 mg |
| lactose | 75 mg |

EXAMPLE 20

The sucrose, calcium sulfate dihydrate and Formula (I) compound shown in Table III below, are mixed and granulated with a 10% gelatin solution. The wet granules are screened, dried, mixed with the starch, talc and stearic acid, screened and compressed into a tablet.

TABLE III

| Ingredients | Amounts |
| --- | --- |
| 6-chloro-2,3,4,5,-tetrahydro-3-methyl-9-(1H-pyrazol-1-ylmethoxy)-1H-3-benzazepine | 100 mg |
| calcium sulfate dehydrate | 150 mg |
| sucrose | 20 mg |
| starch | 10 mg |
| talc | 5 mg |
| stearic acid | 3 mg |

EXAMPLE 21

6-Chloro-9-(3-furanylmethoxy)2,3,4,5-tetrahydro-3-methyl-1H-3-benzazepine 75 mg, is dispersed in 25 ml of normal saline to prepare an injectable-preparation.

While the preferred embodiments of the invention are illustrated by the above, the invention is not limited to the precise instructions herein disclosed and that the right to all modifications coming within the scope of the following claims is reserved.

What is claimed is:

1. A method of treating hypertension in mammals which comprises administering to a subject in need thereof an effective amount of a compound having the formula:

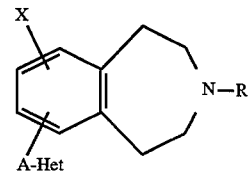

in which:

X is H, Cl, Br, F, I, $CF_3$, $C_{1-6}$alkyl, $COR^1$, $CO^2R^2$, $CONR^2R^2$, CN, $NO_2$, $NR^3R^4$, $OR^3$, $SR^1$, $SCF_3$, or any accessible combination thereof up to three substituents;

R is H, $C_{1-6}$alkyl, or $C_{3-5}$alkenyl;

A is $-OCO(CH_2)_{1-4}-$, $-OCH_2CH=CH-$, $-CO_2(CH_2)_{1-4}-$, $-(CH_2)_{0-6}-$, or $-(CH_2)_nZ(CH_2)_m-$, wherein n is 0–4 and m is 1–5, with the proviso that m and n taken together are no greater than 5;

Z is O;

each $R^1$ independently is $C_{1-6}$alkyl or $(CH_2)_{0-6}$phenyl;

each $R^2$ independently is H, $C_{1-6}$alkyl, or $(CH_2)_{0-6}$phenyl;

$R^3$ is H, $C_{1-6}$alkyl, CHO, $COR^1$, or $SO_2R^1$;

$R^4$ is H or $C_{1-6}$alkyl; and

Het is a heteroaryl group selected from thienyl, furanyl, pyrazolyl, imidazolyl, pyrrolyl, triazolyl, oxazolyl, isoxazolyl, oxadiazolyl, thiadiazolyl, pyridazinyl, pyrimidinyl, thiazolyl, pyridinyl, or tetrazolyl which are unsubstituted or substituted by $C_{1-6}$alkyl, $C_{1-6}$alkoxy, Cl, Br, F, I, $NR^3R^4$, $CO_2R^2$, $CONR^2R^2$, CN, or $NO_2$; or a pharmaceutically acceptable salt thereof.

2. A method according to claim 1 of the formula (Ia):

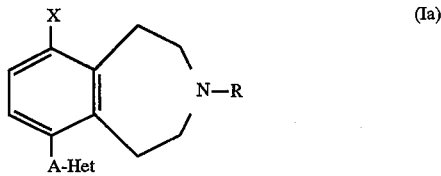

in which:

X is H, Cl, Br, F, I, $CF_3$, $C_{1-6}$alkyl, $COR^1$, $CO2R^2$, $CONR^2R^2$, CN, $NO_2$, $NR^3R^4$, $OR^3$, $SR^1$, $SCF_3$, or any accessible combination thereof up to three substituents;

R is H, $C_{1-6}$alkyl, or $C_{3-5}$alkenyl;

A is $-OCO(CH_2)_{1-4}-$, $-OCH_2CH=CH-$, $-CO_2(CH_2)_{1-4}-$, $-(CH_2)_{0-6}-$, or $-(CH_2)_nZ(CH_2)_m-$, wherein n is 0–4 and m is 1–5, with the proviso that m and n taken together are no greater than 5;

Z is O;

each $R^1$ independently is $C_{1-6}$alkyl or $(CH_2)_{0-6}$phenyl;

each $R^2$ independently is H, $C_{1-6}$alkyl, or $(CH_2)_{0-6}$phenyl;

$R^3$ is H, $C_{1-6}$alkyl, CHO, $COR^1$, or $SO_2R^1$;

$R^4$ is H or $C_{1-6}$alkyl; and

Het is a heteroaryl group selected from thienyl, furanyl, pyrazolyl, imidazolyl, pyrrolyl, triazolyl, oxazolyl, isoxazolyl, oxadiazolyl, thiadiazolyl, pyridazinyl, pyrimidinyl, thiazolyl, pyridinyl, or tetrazolyl which are unsubstituted or substituted by $C_{1-6}$alkyl, $C_{1-6}$alkoxy, Cl, Br, F, I, $NR^3R^4$, $CO_2R^2$, $CONR^2R^2$, CN, or $NO_2$; or a pharmaceutically acceptable salt thereof.

3. A compound of claim 2 wherein X is Cl, Br, F, or I.

4. A compound of claim 3 wherein Het is pyrazolyl, furanyl, thienyl, triazolyl, pyridinyl, or pyrrolyl with each heteroaryl group being unsubstituted or substituted by Cl or $CH_3$.

5. A compound of claim 4 wherein R is $CH_3$.

6. A compound of claim 5 which is 6-chloro-9-(3-furanylmethoxy)-2,3,4,5-tetrahydro-3-methyl-1H-3-benzazepine or a pharmaceutically acceptable salt thereof.

7. A compound of claim 5 which is:

6-chloro-2,3,4,5-tetrahydro-3-methyl-9-(1H-pyrazol-1-ylmethoxy)-1H-3-benzazepine;

6-chloro-9-(4-chloro-1H-pyrazol-1-ylmethoxy)-2,3,4,5-tetrahydro-3-methyl-1H-3-benzazepine;

6-chloro-9-(2-furanylmethoxy)-2,3,4,5-tetrahydro-3-methyl-1H-3-benzazepine;

6-chloro-9-[3-(2-furanyl)-2-propenyloxy]-2,3,4,5-tetrahydro-3-methyl-1H-3-benzazepine;

6-chloro-2,3,4,5-tetrahydro-3-methyl-9-(2-thienylmethoxy)-1H-3-benzazepine;

6-chloro-2,3,4,5-tetrahydro-3-methyl-9-(3-thienylmethoxy)-1H-3-benzazepine;

6-chloro-2,3,4,5-tetrahydro-3-methyl-9-[2-(1H-pyrazol-1-yl)ethoxy]-1H-3-benzazepine;

6-chloro-2,3,4,5-tetrahydro-3-methyl-9-(1H-1,2,4-triazol-1-ylmethoxy)-1H-3-benzazepine;

6-chloro-2,3,4,5-tetrahydro-3-methyl-9-(4-pyridinylmethoxy)-1H-3-benzazepine;

6-chloro-2,3,4,5-tetrahydro-3-methyl-9-[2-(1H-1,2,4-triazol-1-yl)ethoxy]-1H-3-benzazepine;

6-chloro-9-[(4-chloro-1H-pyrazol-1-ylmethoxy)-methyl]-2,3,4,5-tetrahydro-3-methyl-1H-3-benzazepine;

6-chloro-9-[(4-chloro-1H-pyrazol-1-ylmethoxy)-carbonyl]-2,3,4,5-tetrahydro-3-methyl-1H-3-benzazepine;

6-chloro-2,3,4,5-tetrahydro-3-methyl-9-(1H-pyrrol-1-yl)-1H-3-benzazepine;

6-chloro-9-(2,5-dimethyl-1H-pyrrol-1-yl)-2,3,4,5-tetrahydro-3-methyl-1H-3-benzazepine;

6-chloro-2,3,4,5-tetrahydro-3-methyl-9-(1H-pyrrol-1-ylmethyl)-1H-3-benzazepine;

6-chloro-9-[3-(4-chloro-1H-pyrazol-1-yl)propyl]-2,3,4,5-tetrahydro-3-methyl-1H-3-benzazepine; or 6-chloro-9-[5-(4-chloro-1H-pyrazol-1-yl)pentyl]-2,3,4,5-tetrahydro-3-methyl-1H-3-benzazepine; or a pharmaceutically acceptable salt thereof.

* * * * *